United States Patent
Tang et al.

(10) Patent No.: US 12,351,840 B2
(45) Date of Patent: Jul. 8, 2025

(54) CPF1 PROTEIN AND ITS USE IN GENE EDITING

(71) Applicant: ZHEJIANG LAB, Hangzhou (CN)

(72) Inventors: Jin Tang, Hangzhou (CN); Junchao Shi, Hangzhou (CN); Yuanyuan Feng, Hangzhou (CN); Peixiang Ma, Hangzhou (CN); Xingxu Huang, Hangzhou (CN)

(73) Assignee: HANGZHOU LUCA INTELLIGENT TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 18/658,938

(22) Filed: May 8, 2024

(65) Prior Publication Data
US 2025/0002882 A1    Jan. 2, 2025

(30) Foreign Application Priority Data
Mar. 10, 2023   (CN) .......................... 202310258665.1

(51) Int. Cl.
| | | |
|---|---|---|
| *C12N 9/22* | (2006.01) | |
| *C12N 1/21* | (2006.01) | |
| *C12N 15/11* | (2006.01) | |
| *C12N 15/63* | (2006.01) | |

(52) U.S. Cl.
CPC .............. *C12N 9/22* (2013.01); *C12N 15/111* (2013.01); *C12N 15/63* (2013.01); *C12N 2310/20* (2017.05); *C12N 2800/22* (2013.01)

(58) Field of Classification Search
None
See application file for complete search history.

(56) References Cited

U.S. PATENT DOCUMENTS

| | | |
|---|---|---|
| 2019/0010481 A1 | 1/2019 | Joung et al. |
| 2021/0009974 A1* | 1/2021 | Harrington .......... C12N 15/113 |
| 2023/0040148 A1 | 2/2023 | Beaudoin et al. |

FOREIGN PATENT DOCUMENTS

| | | |
|---|---|---|
| CN | 109312316 A | 2/2019 |
| CN | 110799525 A | 2/2020 |
| CN | 111712569 A | 9/2020 |
| CN | 113136376 A | 7/2021 |
| CN | 116179511 A | 5/2023 |
| WO | WO2021178717 | 9/2021 |

OTHER PUBLICATIONS

Xingxu Huan (Novel CRISPR-Cas12a Clades Discovery Using Large Language Model, 2024, Research Square, doi.org/10.21203/rs.3.rs-4817511/v1. (Year: 2024).*
Shmakov et al., Discovery and Functional Characterization of Diverse Class 2 CRISPR-Cas Systems, Molecular Cell 60, 2015, 385-97. (Year: 2015).*
Wang, Xinjie et al., Rapid and sensitive detection of COVID-19 using CRISPR/Cas 12a-based detection . . . , Science Bulletin 65 (2020)1436-1439.
Liu, Ke et al., Mining, engineering and functional expansion of CRISPR/Cas systems, Synthetic Biology Journal, 2023.4(1): 47-66.

* cited by examiner

*Primary Examiner* — Todd M Epstein
(74) *Attorney, Agent, or Firm* — Jiwen Chen; Joywin IP Law PLLC (57) ABSTRACT

The present invention discloses a Cpf1 protein and its use in gene editing, which relates to the field of biotechnology. The present invention provides a Cas12a nuclease named as the Cas12a-68 protease, which has a wider PAM recognition range than traditional nucleases and is capable of recognizing targets of various genes. When editing nucleic acid fragments, using the new nuclease of the present invention is capable of overcoming the shortcomings of the traditional Cas12a and increasing the PAM recognition range. These advantages make the present invention more suitable for editing a wider range of nucleic acid fragments and lay a foundation for gene editing applications.

3 Claims, 3 Drawing Sheets
Specification includes a Sequence Listing.

SEQUENCE LISTING

```
Sequence total quantity: 20
SEQ ID NO: 1            moltype = AA  length = 1293
FEATURE                 Location/Qualifiers
source                  1..1293
                        mol_type = protein
                        organism = synthetic construct
SEQUENCE: 1
MRTMVTFENF TKQYQVSKTL RFELIPQGKT LENMKRDGII SVDRQRNDDY QKAKGILDKL   60
YKYILDSTME TAVIDWEELA IAIEEFRKSK DKKTYEKVQS KVRTALLEHV KKQKVGTEDL  120
FKGMFSSKII TGEVLAAFPE IRLSDEENLI LEKFKDFTTY FTGFFENRKN VFTDEALSTS  180
FTYRLVNDNF IKFFDNCTVM KNVVNISPDM AKSLETCVSD LGIFPGVSLE EVFSVSFYNR  240
LLTQTGIDQF NQLLGGISGK EGEYKKQGLN EIINLAMQQS PEVKEVLKNK AHRFTPLFKQ  300
ILSDRSTMSF IPDAFADDDE VLSAVDAYRK YLLEKNIGDR AFQLISDIEE YSPELMRIGG  360
KYVSVLSQLL FNSWSEIRDG VKAYKESLIT GKKTKKELEN IDKGIKYGVT LQEIKEALPK  420
KDIYEEVKKY AMSVVKDYHA GLAEPLPEKI ETDDERASIK HIMDSMLGLY RFLEYFSHDS  480
IEDTDPVFGE CLDTILDDMN ETVPLYNKVR NFSTRKVYST EKFKLNFNNS SLANGWDKNK  540
EQANGAVLLK KAGEYFLGIF NSKNKPKLVS DGGGGTGYEK MIYKQFPDFK KMLPKCTISR  600
KETKAHFQKS DEDFTLLTDK FEKSLVITKK IYDLGTQTVN GKKKFQVDYP RLTGDMEGYR  660
AALKEWIDFG KKFIQAYAST AIYDTSLFRN SSDYPDLPSF YKDVDNICYK LTFECIPDAV  720
INDCIDDGSL YLFKLHNKDF SAGSIGKPNL HTLYWKAIFE EENLSDVVVK LNGQAELFYR  780
PKSLTRPVVH EAGEVIINKT TSTGLPVPDD VYVELSKFVR NGKKGNLTDK AKNWLDKVTV  840
RKTPHAIIKD RRFTVDKFFF HVPITLNYKA DSSPYRFNDF VRQYVKDCSD VNIIGIDRGE  900
```

```
RNLIYAVVID GKGNIIEQRS FNTVGTYNYQ EKLEQKEKER QTARQDWATV TKIKDLKKGY    960
LSAVVHELSK MIVKYKAIVV LENLNVGFKR MRGGIAERSV YQQFEKALID KLNYLVFKDE   1020
EQSGYGGVLN AYQLTDKFES FSKMGQQTGF LFYVPAAYTS KIDPLTGFIN PFSWKHVKNR   1080
EDRRNFLNLF SKLYYDVNTH DFVLAYHHSN KDSKYTIKGN WEIADWDILI QENKEVFGKT   1140
GTPYCVGKRI VYMDDSTTGH NRMCAYYPHT ELKKLLSEYG IEYTSGQDLL KIIQEFDDDK   1200
LVKGLFYIIK AALQMRNSNS ETGEDYISSP IEGRPGICFD SRAEADTLPH NADANGAFHI   1260
AMKGLLLTER IRNDDKLAIS NEEWLNYIQE MRG                                1293

SEQ ID NO: 2           moltype = DNA  length = 3879
FEATURE                Location/Qualifiers
source                 1..3879
                       mol_type = other DNA
                       organism = synthetic construct
SEQUENCE: 2
atgcgtacta tggtaacgtt cgagaacttc accaaacaat atcaggtctc taagacgttg     60
cgtttcgaac ttatccctca aggcaaaaca ttagagaata tgaaacgtga cggtattatt    120
agtgtggacc gccaacgcaa cgacgattat cagaaggcta aaggcatctt ggacaagtta    180
tacaagtaca ttttagattc aacgatggag acagcggtga tcgattggga ggaactggcc    240
attgcaatcg aggagttccg taaatcaaag gataaaaaga catacgaaaa ggttcaatca    300
aaggtccgca ctgccctttt ggagcatgtc aagaaacaga aagtgggcac agaggacttg    360
tttaaaggga tgttcagttc aaaaattatt acaggagaag tcttggcagc atttcctgag    420
attcgtttat ctgacgagga gaatcttatt ttagagaagt ttaaagactt cactacataa    480
tttactggat tcttcgaaaa ccgtaaaaat gttttcactg acgaagcctt gagcactagc    540
ttcacttatc gtcttgtgaa tgacaatttc atcaaatttt tcgataattg cactgtgatg    600
aaaaacgttg tgaacatctc gcccgacatg gcgaagtccc ttgagacatg cgtcagcgac    660
ttaggtattt tcccgggtgt ttccttagag gaagtgtttc cggtcagttt ttataatggc    720
cttctgacac aaacaggcat tgatcaattt aaccaattat taggcggcat ttctggcaag    780
gaaggcgaat ataagaagca aggactgaac gagatcatca atttggcgat gcagcaatcc    840
cctgaagtta aggaggtttt gaagaacaag gcccaccgct ttacacccct tttcaaacaa    900
attttatcgg atcgttcgac aatgagtttc atcccgacg cgtttgctga cgatgataa     960
gttcttcag ccgtgacgc atatcgtaag tatcttcttg aaaaaaatat cggtgaccgc    1020
gcctttcagt taatttcgga cattgaggag tactcacctg agttaatgcg catcgggggc    1080
aagtatgtta gtgttttgag ccaattgttg tttaactcat ggtctgagat ccgtgatggg    1140
gtgaaggcat ataaggaatc actgcgtgact ggaaaaaaaa caaagaaaga gttggaaaac    1200
attgacaagg gtatcaagta cggcgtgact cttcaggaaa tcaaggaagc tttaccaaaa    1260
aaagatattt cgaggaggt gaagaaatac gcgatgtccg tagtaaaaga ctatcatgcc    1320
ggcttagctg aaccgttgcc agaaaaaatc gaaacgacg acgaacgtgc atccatcaaa    1380
catattatgg attcaatgct gggactgtac cgcttcttag aatatttctc gcatgacagc    1440
attgaggaca ctgaccagt ttttggagaa tgcctggata caattcttga tgacatgaac    1500
gagaccgttc ctttgtataa caaggttcgc aatttctcga ctcgtaaggt atattctaca    1560
gaaaagttca aattaaactt taacaactca agtttggcaa acggatggga taaaaataaa    1620
gaacaagcta atggtgctgt cctctgaaa aaggcggggg agtatttctt aggcatcttc    1680
aattctaaga acaagcccaa gctggtatcc gatggagtg gaggtacagg ctatgaagaa    1740
atgatctata agcagtttcc cgatttttag aagatgttac ctaaatgtac aatcagccgc    1800
aaagagacaa aagcgcattt ccagaaatcg gacgaagact tcacgttatt aacagacaaa    1860
tttgagaaga gcctggtaat taccaaaaag atctatgatt taggcactca aacggtcaac    1920
ggaaagaaa agtttcaagt cgactacccg cgccttaccg gggatatgga gggtaccgc    1980
gctgcactga agaatggat cgattttgga aagaaattta ttcaagccta cgcgtccact    2040
gcgatctatg atacttccct gtttcgtaat tcctccgatt atcctgactt gccatcattc    2100
tacaaagatg ttgataacat ctgttataaa ttaactttcg aatgtattcc agacgcagtc    2160
attaatgatt gtatcgacga cgggagcttg tacttattca aattgcacaa taaggacttc    2220
tcggccgggt ccattggcaa gccgaacctg catactcttt actggaaagc gatctttgag    2280
gaagagaatc tttcggatgt ggtagtcaaa ttgaatggtc aggccgagtt gttctatcgt    2340
cccaaatcac tgacgcgccc agtagttcat gaggctggtg aggtgattat caacaagacg    2400
acaagcactg gtttacctgt tccagatgac gtctacgtcg agctttccaa atttgttcgc    2460
aacggtaaaa aaggtaattt aacggacaaa gctaagaatt ggcttgacaa ggtgactgtc    2520
cgtaagacgc cccacgcgat tatcaaagat cgtcgcttca ctgtagacaa gttcttcttc    2580
cacgtgccaa ttactcttaa ttacaaggcg gattcatccc cttatcgctt taatgatttt    2640
gtgcgtcagt acgtgaagga ctgctctgat gtgaacatta tcggcatcga tcgtggcgag    2700
cgtaatctta tctatgcagt cgttatcgac ggaaagggta atatcattga gcagcgcagg    2760
tttaacaccg tagggacata taactatcag gaaaaattgg aacaaaagga gaagaacgt    2820
cagactgcac gccaagattg ggccaccgta accaaaatta aggacctgaa aaagggtac    2880
ctgtcagcgg tggttcatga acttagcaag atgattgtaa agtataaggc aatcgtggtc    2940
cttgaaaatt taaacgtggg gttcaaacgt atgcgtggta gaattcgaga acgttctgtt    3000
taccagcagt ttgagaaggc gttgatcgat aaattgaatt atttggtgtt taaggacgaa    3060
gaacaatcag gttacggtgg cgtgttaaac gcgtatcagc ttacagacaa gttcgagagt    3120
ttcagcaaga tgggccaaca gaccgggttt ttattctacg ttcccgccgc atacacgtca    3180
aagatcgatc cactgaccgg cttcattaac ccttttcagct ggaaacatgt aaaaaaccgc    3240
gaagaccgcc gcaacttttt gaacctgttc agcaaactgt attatgatgt caacacacac    3300
gattttgtac ttgcgtacca ccattccaac aaagattcaa aatatacaat caaaggaaat    3360
tgggaaatcg ctgactggga tatcctgatt caagagaaca aagaggtgtt cggtaagacg    3420
gggacgccgt actgcgtcgg aaagcgcatt gtttatatgg atgattcgac gacaggccac    3480
aaccgtatgt gtgcttacta tccgcacacc gagttaaaaa aacttctgag cgaatacggt    3540
attgagtaca catctggcca agatttttta aagattattc agtagaattga tgacgacaaa    3600
ttggtcaaag gcttgtttta tatcattaaa gcgcgctgc aaatgcgtaa cagcaatagt    3660
gagacaggcg aagattacat ttcatcccct atcgagggcc gccaggaat tgtttttgac    3720
tcgcgcgcag aggcggacac attacctcac aacgccgacg ccaatggagc cttccacatc    3780
gcgatgaagg ggttgttgct tacagaacgt attcgcaatg atgataaatt agcaatttct    3840
aatgaggagt ggctgaacta catccaagag atgcgtggg                           3879
```

```
SEQ ID NO: 3              moltype = DNA  length = 299
FEATURE                   Location/Qualifiers
source                    1..299
                          mol_type = genomic DNA
                          organism = unidentified
                          note = coronaviridae(middle east respiratory
                            syndrome-related coronavirus)
SEQUENCE: 3
ccatgggcta ccatgctgtt ttcgtgcctg caacgcgcga ttcagttcct cttcacataa    60
tcgccccgag ctcgcttatc gtttaagcag ctctgcgcta ctatgggtcc cgtgtagagg   120
ctaatccatt agtctctctt tggacatatg gaaaacgaac tatgttaccc tttgtccaag   180
aacgaatagg gttgttcata gtaaactttt tcattttttac cgtagtatgt gctataaac   240
tcttggtgtg tatggctttc cttacggcta ctagattatg tgtgtttttt tgagaattc    299

SEQ ID NO: 4              moltype = AA  length = 1293
FEATURE                   Location/Qualifiers
source                    1..1293
                          mol_type = protein
                          organism = synthetic construct
SEQUENCE: 4
MRTMVTFENF TKQYQVSKTL RFELIPQGKT LENMKRDGII SVDRQRNDDY QKAKGILDKL    60
YKYILDSTME TAVIDWEELA IAIEEFRKSK DKKTYEKVQS KVRTALLEHV KKQKVGTEDL   120
FKGMFSSKII TGEVLAAFPE IRLSDEENLI LEKFKDFTTY FTGFFENRKN VFTDEALSTS   180
FTYRLVNDNF IKFFDNCTVM KNVVNISPDM AKSLETCVSD LGIFPGVSLE EVFSVSFYNR   240
LLTQTGIDQF NQLLGGISGK EGEYKKQGLN EIINLAMQQS PEVKEVLKNK AHRFTPLFKQ   300
ILSDRSTMSF IPDAFADDDE VLSAVDAYRK YLLEKNIGDR AFQLISDIEE YSPELMRIGG   360
KYVSVLSQLL FNSWSEIRDG VKAYKESLIT GKKTKKELEN IDKGIKYGVT LQEIKEALPK   420
KDIYEEVKKY AMSVVKDYHA GLAEPLPEKI ETDDERASIK HIMDSMLGLY RFLEYFSHDS   480
IEDTDPVFGE CLDTILDDMN ETVPLYNKVR NFSTRKVYST EKFKLNFNNS SLANGWDKNK   540
EQANGAVLLK KAGEYFLGIF NSKNKPKLVS DGGGGTGYEK MIYKQFPDFK KMLPKCTISR   600
KETKAHFQKS DEDFTLLTDK FEKSLVITKK IYDLGTQTVN GKKKFQVDYP RLTGDMEGYR   660
AALKEWIDFG KKFIQAYAST AIYDTSLFRN SSDYPDLPSF YKDVDNICYK LTFECIPDAV   720
INDCIDDGSL YLFKLHNKDF SAGSIGKPNL HTLYWKAIFE EENLSDVVVK LNGQAELFYR   780
PKSLTRPVVH EAGEVIINKT TSTGLPVPDD VYVELSKFVR NGKKGNLTDK AKNWLDKVTV   840
RKTPHAIIKD RRFTVDKFFF HVPITLNYKA DSSPYRFNDF VRQYVKDCSD VNIIGIARGE   900
RNLIYAVVID GKGNIIEQRS FNTVGTYNYQ EKLEQKEKER QTARQDWATV TKIKDLKKGY   960
LSAVVHELSK MIVKYKAIVV LENLNVGFKR MRGGIAERSV YQQFEKALID KLNYLVFKDE  1020
EQSGYGGVLN AYQLTDKFES FSKMGQQTGF LFYVPAAYTS KIDPLTGFIN PFSWKHVKNR  1080
EDRRNFLNLF SKLYYDVNTH DFVLAYHHSN KDSKYTIKGN WEIADWDILI QENKEVFGKT  1140
GTPYCVGKRI VYMDDSTTGH NRMCAYYPHT ELKKLLSEYG IEYTSGQDLL KIIQEFDDDK  1200
LVKGLFYIIK AALQMRNSNS ETGEDYISSP IEGRPGICFD SRAEADTLPH NADANGAFHI  1260
AMKGLLLTER IRNDDKLAIS NEEWLNYIQE MRG                               1293

SEQ ID NO: 5              moltype = AA  length = 1293
FEATURE                   Location/Qualifiers
source                    1..1293
                          mol_type = protein
                          organism = synthetic construct
SEQUENCE: 5
MRTMVTFENF TKQYQVSKTL RFELIPQGKT LENMKRDGII SVDRQRNDDY QKAKGILDKL    60
YKYILDSTME TAVIDWEELA IAIEEFRKSK DKKTYEKVQS KVRTALLEHV KKQKVGTEDL   120
FKGMFSSKII TGEVLAAFPE IRLSDEENLI LEKFKDFTTY FTGFFENRKN VFTDEALSTS   180
FTYRLVNDNF IKFFDNCTVM KNVVNISPDM AKSLETCVSD LGIFPGVSLE EVFSVSFYNR   240
LLTQTGIDQF NQLLGGISGK EGEYKKQGLN EIINLAMQQS PEVKEVLKNK AHRFTPLFKQ   300
ILSDRSTMSF IPDAFADDDE VLSAVDAYRK YLLEKNIGDR AFQLISDIEE YSPELMRIGG   360
KYVSVLSQLL FNSWSEIRDG VKAYKESLIT GKKTKKELEN IDKGIKYGVT LQEIKEALPK   420
KDIYEEVKKY AMSVVKDYHA GLAEPLPEKI ETDDERASIK HIMDSMLGLY RFLEYFSHDS   480
IEDTDPVFGE CLDTILDDMN ETVPLYNKVR NFSTRKVYST EKFKLNFNNS SLANGWDKNK   540
EQANGAVLLK KAGEYFLGIF NSKNKPKLVS DGGGGTGYEK MIYKQFPDFK KMLPKCTISR   600
KETKAHFQKS DEDFTLLTDK FEKSLVITKK IYDLGTQTVN GKKKFQVDYP RLTGDMEGYR   660
AALKEWIDFG KKFIQAYAST AIYDTSLFRN SSDYPDLPSF YKDVDNICYK LTFECIPDAV   720
INDCIDDGSL YLFKLHNKDF SAGSIGKPNL HTLYWKAIFE EENLSDVVVK LNGQAELFYR   780
PKSLTRPVVH EAGEVIINKT TSTGLPVPDD VYVELSKFVR NGKKGNLTDK AKNWLDKVTV   840
RKTPHAIIKD RRFTVDKFFF HVPITLNYKA DSSPYRFNDF VRQYVKDCSD VNIIGIDRGE   900
RNLIYAVVID GKGNIIEQRS FNTVGTYNYQ EKLEQKEKER QTARQDWATV TKIKDLKKGY   960
LSAVVHELSK MIVKYKAIVV LANLNVGFKR MRGGIAERSV YQQFEKALID KLNYLVFKDE  1020
EQSGYGGVLN AYQLTDKFES FSKMGQQTGF LFYVPAAYTS KIDPLTGFIN PFSWKHVKNR  1080
EDRRNFLNLF SKLYYDVNTH DFVLAYHHSN KDSKYTIKGN WEIADWDILI QENKEVFGKT  1140
GTPYCVGKRI VYMDDSTTGH NRMCAYYPHT ELKKLLSEYG IEYTSGQDLL KIIQEFDDDK  1200
LVKGLFYIIK AALQMRNSNS ETGEDYISSP IEGRPGICFD SRAEADTLPH NADANGAFHI  1260
AMKGLLLTER IRNDDKLAIS NEEWLNYIQE MRG                               1293

SEQ ID NO: 6              moltype = RNA  length = 44
FEATURE                   Location/Qualifiers
source                    1..44
                          mol_type = other RNA
                          organism = synthetic construct
SEQUENCE: 6
```

-continued

```
taatttctac taagtgtaga tgacatatgg aaaacgaact atgt            44

SEQ ID NO: 7            moltype = RNA   length = 41
FEATURE                 Location/Qualifiers
source                  1..41
                        mol_type = other RNA
                        organism = synthetic construct
SEQUENCE: 7
taatttctac taagtgtaga tccggttccg gcaccgggct t                41

SEQ ID NO: 8            moltype = RNA   length = 41
FEATURE                 Location/Qualifiers
source                  1..41
                        mol_type = other RNA
                        organism = synthetic construct
SEQUENCE: 8
taatttctac taagtgtaga tggacatcga agaagacatc c                41

SEQ ID NO: 9            moltype = RNA   length = 41
FEATURE                 Location/Qualifiers
source                  1..41
                        mol_type = other RNA
                        organism = synthetic construct
SEQUENCE: 9
taatttctac taagtgtaga tccagagcat cccgtggaac g                41

SEQ ID NO: 10           moltype = RNA   length = 41
FEATURE                 Location/Qualifiers
source                  1..41
                        mol_type = other RNA
                        organism = synthetic construct
SEQUENCE: 10
taatttctac taagtgtaga tgatgtcttc ttcgatgtcc a                41

SEQ ID NO: 11           moltype = DNA   length = 289
FEATURE                 Location/Qualifiers
source                  1..289
                        mol_type = other DNA
                        organism = synthetic construct
SEQUENCE: 11
gccttcctgg agacctccgc gccccgcaac ctccccttct acgagcggct cggcttcacc      60
gtcaccgccg acgtcgaggt gcccgaagga ccgcgcacct ggtgcatgac ccgcaagccc     120
ggtgccgaa ccggtnnntg gacatcgaag aagacatccn nncccagagc atcccgtgga     180
acgtaactgg atccggcgca acaaacttct ctctgctgaa acaagccgga gatgtcgaag     240
agaatcctgg actggtgagc aagggcgagg agctgttcac cggggtggt                289

SEQ ID NO: 12           moltype = DNA   length = 26
FEATURE                 Location/Qualifiers
source                  1..26
                        mol_type = other DNA
                        organism = synthetic construct
SEQUENCE: 12
agtcaaaacc tccccttcta cgagcg                                 26

SEQ ID NO: 13           moltype = DNA   length = 20
FEATURE                 Location/Qualifiers
source                  1..20
                        mol_type = other DNA
                        organism = synthetic construct
SEQUENCE: 13
agctcctcgc ccttgctcac                                        20

SEQ ID NO: 14           moltype = DNA   length = 26
FEATURE                 Location/Qualifiers
source                  1..26
                        mol_type = other DNA
                        organism = synthetic construct
SEQUENCE: 14
acttgaagct cctcgccctt gctcac                                 26

SEQ ID NO: 15           moltype = DNA   length = 26
FEATURE                 Location/Qualifiers
source                  1..26
                        mol_type = other DNA
                        organism = synthetic construct
SEQUENCE: 15
gatcagagct cctcgccctt gctcac                                 26

SEQ ID NO: 16           moltype = DNA   length = 26
```

```
FEATURE              Location/Qualifiers
source               1..26
                     mol_type = other DNA
                     organism = synthetic construct
SEQUENCE: 16
tagcttagct cctcgccctt gctcac                                             26

SEQ ID NO: 17        moltype = DNA  length = 39
FEATURE              Location/Qualifiers
source               1..39
                     mol_type = other DNA
                     organism = synthetic construct
SEQUENCE: 17
tgtgaacatt atcggcatcg ctcgtggcga gcgtaatct                               39

SEQ ID NO: 18        moltype = DNA  length = 38
FEATURE              Location/Qualifiers
source               1..38
                     mol_type = other DNA
                     organism = synthetic construct
SEQUENCE: 18
cgatgccgat aatgttcaca tcagagcagt ccttcacg                                38

SEQ ID NO: 19        moltype = DNA  length = 39
FEATURE              Location/Qualifiers
source               1..39
                     mol_type = other DNA
                     organism = synthetic construct
SEQUENCE: 19
taaggcaatc gtggtccttg caaatttaaa cgtggggtt                               39

SEQ ID NO: 20        moltype = DNA  length = 38
FEATURE              Location/Qualifiers
source               1..38
                     mol_type = other DNA
                     organism = synthetic construct
SEQUENCE: 20
caaggaccac gattgcctta tactttacaa tcatcttg                                38
```

CPF1 PROTEIN AND ITS USE IN GENE EDITING

This application claims priority of Chinese Application No. 202310258665.1, filed Mar. 10, 2023, which is hereby incorporated by reference.

FIELD OF TECHNOLOGY

The present invention relates to the field of biotechnology, in particular to a Cpf1 protein and its use in gene editing.

BACKGROUND TECHNOLOGY

Gene editing technology enables the modification of DNA sequence loci, such as with the first-generation gene editing tool, zinc finger nucleases (ZFNs), and the second-generation tool, transcription activator-like effector nucleases (TALENs), can both be used to modify targeted genomes, but these methods are difficult to design, not easy to manufacture, expensive, and not universal.

CRISPR-Cas systems originate from the RNA-guided adaptive immune systems of bacteria, initially utilized to combat nucleic acid invaders such as bacteria and archaea. CRISPR refers to clustered regularly interspaced short palindromic repeats, which are derived from phage DNA fragments that are capable of infecting prokaryotes. CRISPR are capable of detecting and destroying similar DNA in other phages that can cause similar infections, so they are critical for prokaryotes to resist phages. Therefore, the sequence is the immune system of many prokaryotes. Cas proteins refer to CRISPR-associated proteins, which are associated proteins in CRISPR systems. A CRISPR locus consists of an operon encoding a Cas protein and a repeat spacer, which can be guided by RNA corresponding to the spacer in the CRISPR sequence, to recognize and cleave specific DNA strands complementary to its sequence. The CRISPR/Cas9 system belongs to the class 2 CRISPR system, which consists of Cas9 nuclease, crRNA and tracrRNA, and is the most widely used gene editing tool currently; this system is simple and efficient, and only needs to synthesize a new segment of RNA to realize gene editing, and its properties of simple design and easy operation have become the greatest advantages, making this technology a convenient and adaptable tool for regulating and observing genomes. This allows the system to be applied in biological research and biotechnology in a wide range of fields, including different fields such as gene regulation, surface modification, base editing, gene imaging and so on, and has shown a wide range of applicability in microorganisms, plants, animals and even human bodies. The CRISPR-Cas tool has greatly accelerated the pace of scientific research, and the research and development of biotechnology based on Cas has also made rapid progress. Several clinical trials leveraging Cas9 are either ongoing or imminent, with their outcomes expected to inform future applications of somatic gene editing in vitro and in clinical settings.

Currently, the CRISPR/Cas system has developed from the initial CRISPR/Cas9 to various gene editing systems such as the present CRISPR/Cas12a, and CRISPR/Cas13a. Among them, CRISPR-Cas12a is a Class 2 RNA-guided endonuclease, which can be used to edit the CRISPR system of mammalian genomes. In September 2015, Zhang Feng's group (Zetsche B, Gootenberg J S, Abudayyeh 0, et al. Cpf1 is a single RNA-guided endonuclease of a class 2 CRISPR-Cas system. *Cell,* 2015, 163(3): 759-771.) added a new member to the CRISPR family-Cpf1, which belongs to type V of the class 2 CRISPR-Cas system. The CRISPR/Cpf1 system belongs to type V of class 2, which is small in size, has the abilities of both RNA endonuclease and DNA endonuclease, and can recognize PAM sequences rich in thymine (T), thus expanding the editable range of the CRISPR/Cas system. The system not only has good activity of targeted cleavage of DNA, but also shows editing characteristics that are significantly different from CRISPR-Cas9. The Cas12a nuclease enlarges the selection range of gene editing target sites, while the off-target effect is lower. Compared with the Cas9 nuclease, the Cas12a nuclease recognizes the DNA target sequences complementary to crRNA spacers without using tracrRNA. Moreover, the Cas12a protease has a smaller molecular weight, and is easier to enter cells, so the editing success rate is higher. Cleavage with a Cpf1 protein only needs the guidance of a single RNA, which can simplify the design and use of gene editing tools. Meanwhile, the system Cpf1 produces the effect of gene editing by recognizing T-rich PAM and leaving a cohesive end in its targeted DNA sequence. The TIC preference of a Cpf1 family protein to recognize PAM extends the range of targeted editing nucleic acids with CRISPR. However, gene editing with a traditional Cas12a protein is limited by the protospacer adjacent motif (PAM), and only a portion of nucleic acid targets can be recognized, for example, LbCas12a tends to recognize the PAM sequence containing TTTV; *Acidaminococcus* Cpf1 (As-Cpf1) and Lachnospiraceae Cpf1 (LbCpf1) are widely used in the world, and because of their lack of flexibility in recognizing the protospacer adjacent motif of 5'-TTTN-3', their application in the field of gene editing is limited. Therefore, it is necessary to find a Cas12a protein or improve the existing Cas12a protein (which refers to a crRNA-dependent endonuclease, also known as the Cpf1 protein, which is a type V enzyme in CRISPR system classification), and find a novel Cas12a protease which has a wider recognition range and is more convenient to use.

SUMMARY OF THE INVENTION

The technical problem to be solved by the present invention is to overcome the defect that the range of PAM of dsDNA target sequences recognized by Cas12a is limited in the prior art. Provided in the present invention is a novel Cas12a nuclease named as the Cas12a-68 protease, which has a wider PAM recognition range than traditional nucleases and is capable of recognizing targets of various genes.

A novel Cas12a nuclease, i.e., a Cpf1 protein, wherein an amino acid sequence of the Cpf1 protein is shown as SEQ ID NO. 1.

Also provided in the present invention is a polynucleotide encoding the Cpf1 protein.

Cpf1 (Cas12a) is capable of recognizing a DNA nucleic acid sequence under the guidance of RNA, but the PAM recognition range of a traditional Cas12a protein is limited, for example, LbCas12a PAM is TTTV, and the novel Cas12a-68 protease we found has a wider PAM recognition range and expands the recognition range.

Preferably, the polynucleotide is codon optimized for expression in a target cell.

Also provided in the present invention is a vector comprising the polynucleotide.

The Cpf1 protein is a codon-optimized Cpf1 protein. The nucleic acid sequences of Cpf1 proteins from different sources are prokaryotic codon optimized to obtain the sequences, constructed into the pET28a expression vector to induce the expression of soluble proteins at low temperature, and purified by affinity purification and molecular sieve purification to obtain the target protein.

Also provided in the present invention is a type V CRISPR/Cas 12a gene editing system, comprising the Cpf1 protein or a polynucleotide encoding the Cpf1 protein.

The type V CRISPR/Cas 12a gene editing system further comprises CRISPR RNA. A sequence of the CRISPR RNA is shown as at least one of SEQ ID NO. 7-10.

Also provided in the present invention is the use of the Cpf1 protein, the polynucleotide, the vector, or the gene editing system in gene editing.

The use is binding to, targeted cleavage or non-targeted cleavage of DNA.

Also provided in the present invention is a gene editing method that utilizes the gene editing system to edit a target DNA.

Specifically, the method includes the following steps:
(1) designing CRISPR RNA for a target gene sequence to be edited;
(2) constructing a gene editing vector comprising an encoding gene sequence of the CRISPR RNA and the polynucleotide; and
(3) introducing the gene editing vector in step (2) into a receptor cell to be gene edited, and screening to obtain a gene edited transgenic cell.

Figure 1:
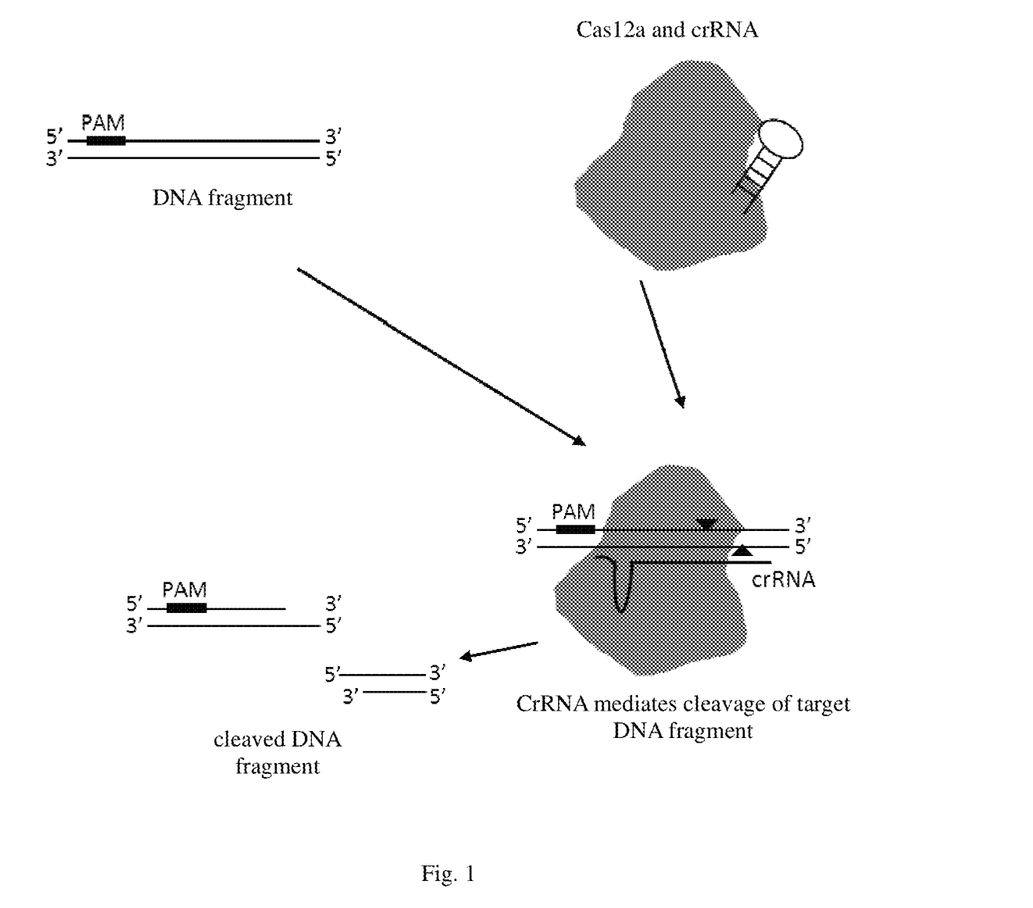
FIG. 1 is a schematic diagram of gene editing with a programmable nuclease.

In the present invention, once a target nucleic acid, crRNA and a Cas12a protein form a ternary complex, the cleavage activity of the Cas12a protease will be activated, and the target DNA will be cleaved by Cas12a. In the presence of suitable PAM, different target DNA fragments can be targeted by designing different crRNA sequences, and the principle is shown in FIG. 1.

In the present invention, the target DNA molecule is inserted into the pET-28a vector and linearized with an EcoR V endonuclease. During the identification experiment of gene editing, in the presence of PAM recognized by the Cas12a protease, the protease will cleave the target DNA molecule from the linearized vector by adding the corresponding crRNA. The reaction system is heated at 95° C. for 5-10 minutes to inactivate the Cas12a protease, and then the target DNA molecule cleaved is observed by agarose gel electrophoresis. Furthermore, we also find that the active sites of the novel Cas12a-68 protease are D897 and E982 by the following analysis: mutating either D897 or E982 of the Cas12a-68 expression vector to alanine, and then assessing whether the mutant can cleave the target dsDNA according to the above steps.

Description of Terms

The term crRNA refers to CRISPR RNA, which is a short RNA that guides Cas12a (Cpf1) to bind to the target DNA sequence.

The term CRISPR refers to clustered regularly interspaced short palindromic repeats, and the sequence is the immune system of many prokaryotes.

The term Cas protein refers to CRISPR-associated proteins, which are associated proteins in CRISPR systems.

The term Cpf1 (also called Cas12a) refers to the crRNA-dependent endonuclease, which is a type V enzyme in CRISPR system classification.

The term PAM refers to the protospacer-adjacent motif, which is necessary for the cleavage with Cas12a. The PAM of FnCas12a is the TTN sequence, and the PAM of LbCas12a is the TTTN sequence.

Based on general knowledge of the art, the preferred conditions above can be arbitrarily combined to obtain various preferred examples of the present invention.

The reagents and raw materials used in the present invention are all commercially available.

The present invention has the following beneficial effects:
Provided in the present invention is a novel Cas12a nuclease named as the Cas12a-68 protease, which has a wider PAM recognition range than traditional nucleases and is capable of recognizing targets of various genes. When editing nucleic acid fragments, using the new nuclease of the present invention is capable of overcoming the shortcomings of the traditional Cas12a and increasing the PAM recognition range. These advantages make the present invention more suitable for editing a wider range of nucleic acid fragments and lay a foundation for gene editing applications.

DESCRIPTION OF THE EMBODIMENTS

The present invention will be further elaborated in combination with specific examples. It should be understood that these examples are only used to illustrate the present invention and are not used to limit the scope of the present invention. Furthermore, it should be understood that after reading the teaching of the present invention, those skilled in the art can make various alterations or modifications to the present invention, and these equivalents also fall within the scope defined by the appended claims of the present application.

The experimental methods for which specific conditions are not specified in the following examples should be selected according to the conventional methods and conditions, or according to the product specifications.

In the present invention, conventional reagents such as Tris-Base (i.e., Tris base, also known as tris(hydroxymethyl) aminomethane), bovine serum albumin (BSA), NaCl, Tris-HCl (i.e., Tris hydrochloride, alias: tris-hydroxymethylaminomethane hydrochloride) and glycerol were purchased from China National Pharmaceutical Group Corporation; the nucleic acid fragments and RNA for detection were synthesized by Beijing Qingke Biotechnology Co., Ltd.; the transfection reagents used to transfect mammalian cells were purchased from Shanghai Li Ji Biotechnology Co., Ltd.; the FALG tag antibody used in the western-blot experiment was purchased from Cell Signaling Technology, Inc (CST); in the experiment, the second-generation sequencing experiment was completed by Annoroad Gene Technology (Beijing) Co., Ltd.; and the cell sorter used in the experiment was an ultra-high speed flow cytometry sorting system (BD FACSAria III).

The gene editing principle of the programmable nuclease provided by the present invention is shown in FIG. 1. Specifically, when a Cas protease recognizes the existence of a PAM sequence, the complex formed by crRNA and the Cas12a protein targets the DNA sequence complementary to the bases of crRNA to open the DNA double strands, and crRNA binds to one of the single strands, i.e., the target strand (TS), at which time the cleavage activity of the Cas12a protease will be activated, and the target strand (TS) and the non-target strand (NTS) will be cleaved by the Cas12a protease. In the presence of suitable PAM, different target DNA fragments can be targeted by designing different crRNA sequences.

The present invention will be further elaborated in combination with specific examples.

Example 1: Cloning and Intracellular Expression of Cas12a-68 Protease

In order to verify whether the novel Cas12a-68 protease has gene editing activity in mammalian cells, it was first verified whether Cas12a-68 was expressed in 293 cells (the human embryonic kidney cell 293, a cell line derived from human embryonic kidney cells).

Wherein, 293 cells have the following characteristics, for example: 1) they have high transfection efficiency; 2) are capable of being cultured in suspension for large-scale expression; 3) the structure of the protein expressed is closest to its conformation in human body; and 4) HEK293 cells can grow rapidly in the culture system and be cultured in high density. 293T cell line is a derivative cell line with high transfection efficiency formed by transfecting a SV40T-antigen gene into 293 cells. This enables the plasmid containing SV40ori to be significantly amplified in this cell line, thus promoting the amplification of expression vectors and the expression of proteins.

Expression of Cas12a-68 protease in HEK293T cells.

The gene fragment (the gene sequence is shown as SEQ ID NO. 2) was cloned, and the amino acid sequence of Cas12a-68 used in the experiment was shown as SEQ ID NO. 1. The gene fragment was amplified by PCR, and the pST1374 vector (Addgene, #13426) was digested by Not I, and then the gene fragment and vector were recombined under the action of recombinase (Vazyme, C112-01). The recombinant plasmid vector was identified by sequencing, and then the plasmid was extracted. The plasmid was transfected into 293 cells by the EZ Trans cell transfection reagent (Li Ji Biotechnology Co., Ltd., AC04L091/AC04L092) and cultured at 37° C. for 48-72 hours. The cells were collected, lysed, and treated by SDS-PAGE protein electrophoresis, and then detected by Western-blot.

Figure 2:
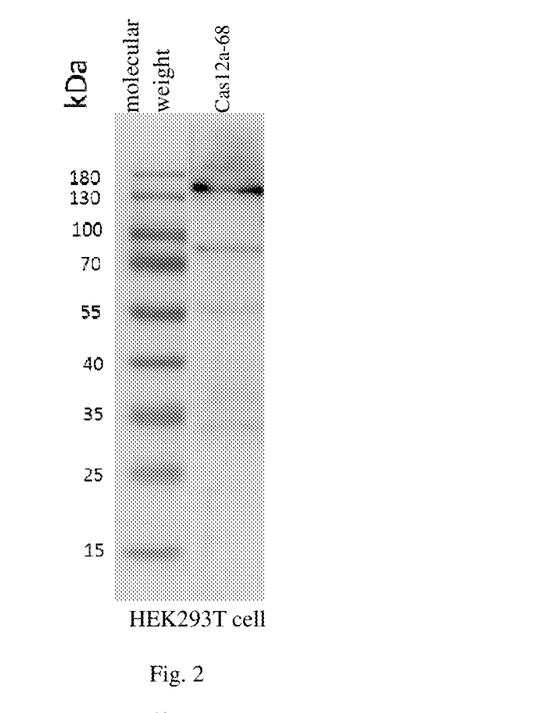
FIG. 2 is a detection diagram of the expression of a programmable nuclease in cells.

The experimental results of the Western-blot detection are shown in FIG. 2. The results show that the Cas12a-68 protein can be expressed in mammalian cells.

Example 2: Cas12a-68 Protease has In Vitro Gene Cleavage Activity

1. Preparation of Nucleic Acid

CrRNAs were synthesized by Beijing Qingke Biotechnology Co., Ltd., and the sequences of crRNAs synthesized are shown in Table 1.

TABLE 1

| crRNA | sequence (5'-3') |
|---|---|
| Mers-cr2+ | UaaUUUcUacUaagUgUagaUGACAUAUGGAAAACGAACUAUGU (SEQ ID. NO. 6) |

2. Detection of Gene Cleavage Activity In Vitro Based on CRISPR/Cas12a

In the experiment, crRNA consisted of a 21 nt region interacting with Cas12a and a 23 nt programmable guiding region for target DNA recognition. The target DNA was a gene fragment of the MERS virus (the sequence used in the experiment was shown as SEQ ID NO. 3). The target DNA fragment was amplified by PCR with forward and backward primers with Nco I and EcoR I enzymes respectively. Then the pET28a vector was double digested by Nco I and EcoR I. The digested vector and the PCR amplification product were reconnected under the action of the T4 ligase, and the ligation product was used to transform DH5a competent cells. The monoclonal strain was selected and cultured by shaking, before collecting the bacteria to extract the plasmid vector. The extracted plasmid was linearized with the EcoR V endonuclease for the detection reaction.

The detection system used was 400 ng of Cas12a-68, 100 ng of target DNA fragments (the gene fragment of MERS virus, the sequence of which was shown as SEQ ID NO. 3), and an amount of 5 pmol of crRNA, with the final volume of the reaction of 10 μL. The reaction was incubated at 37° C. for one hour, and heated at 95° C. for 5-10 minutes to inactivate the Cas12a protease. Then, the target DNA molecule cleaved was observed by agarose gel electrophoresis. After a linearized plasmid is cleaved by Cas, two DNA fragments with lengths of about 4100 bp and 1400 bp will be formed.

Figure 3:
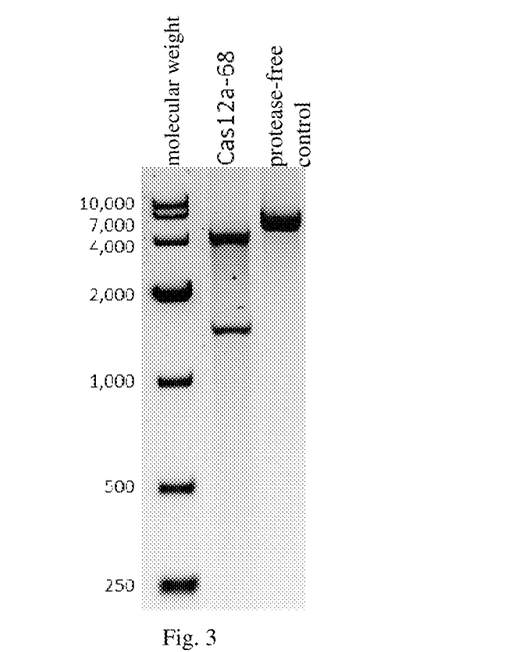
FIG. 3 is a detection diagram of the activity of a programmable nuclease to cleave double-stranded DNA.

In a gene editing system, once crRNA mediates a Cas protease to target a target DNA molecule, the cleavage activity of the protease will be activated, and then the target DNA fragment will be cleaved. The specific experimental results are shown in FIG. 3. From FIG. 3, it can be seen that Cas12a-68 is capable of cleaving double-stranded DNA molecules during the in vitro cleavage activity experiment, indicating that the Cas12a-68 protease has gene editing activity in vitro.

Example 3: Efficiency of Cas12a-68 Protease in Cleaving Fragments Containing Different PAM According to the results of Example 1, the Cas12a-68 protease can be expressed in mammalian cells. This applicant identified whether the protease also had gene editing ability in cells, as well as identified whether different PAM affected the cleavage with the Cas12a-68 protease in cells.

In the experiment, there were four crRNA plasmids, i.e., the libraries where N in NNNN in PAM sequences was A, T, G and C, respectively. The crRNA sequences expressed by the four plasmids are shown in Table 2. In this experiment, crRNA consisted of a 21 nt region interacting with Cas12a and a 20 nt programmable guiding region for target DNA recognition.

TABLE 2

| crRNA | sequence (5'-3') |
|---|---|
| NNNA-crRNA | UaaUUUcUacUaagUgUagaUccggUUccggcaccgggcUU (SEQ ID. NO. 7) |
| NNNT-crRNA | UaaUUUcUacUaagUgUagaUggacatCgaagaagacatcC (SEQ ID. NO. 8) |
| NNNC-crRNA | UaaUUUcUacUaagUgUagaUccagagcaUcccgUggaacG (SEQ ID. NO. 9) |
| NNNG-crRNA | UaaUUUcUacUaagUgUagaUgaUgUcUUcUUcGaUgUccA (SEQ ID. NO. 10) |

The cell lines used in the experiment contained plasmid libraries with different PAM sequences. As shown in Table 3, PAM has TNNN and CNNN, while the complementary chains have different PAM sequences of NNNA and NNNG, where N represents any base, i.e., A, T, G and C.

TABLE 3

| target DNA | sequence (5'-3', where N represents any base) |
|---|---|
| NNNN (the cell plasmid vector cleavage sequence) | gccttcctggagacctccgcgccccgcaacctcccttctacgagcggctcggcttcaccgtcaccgc cgacgtcgaggtgcccgaaggaccgcgcacctggtgcatgacccgcaagcccggtgccggaAcc ggTNNNTggacatCgaagaagacatcCNNNCccagagcatcccgtggaacGTAACT ggatccggcgcaacaaacttctctctgctgaaacaagccggagatgtcgaagagaatcctggacTgg tgagcaagggcgaggagctgttcaccggggtggt (SEQ ID. NO. 11) |

The cell lines used in the experiment contained plasmid libraries with different PAM sequences, and the cleavage region was located in front of the green fluorescent protein (GFP) gene. Because of frame shift mutation (which refers to the change of the reading frame of a DNA molecule due to the deletion or insertion of a base at a certain site, which leads to a series of code changes downstream, so that the gene originally encoding a certain peptide chain becomes a sequence encoding a completely different peptide chain), GFP could not be expressed, and there was no fluorescence under laser. However, in cells, when a Cas12a-68 protease binds to crRNA and targets a gene region with a suitable PAM sequence, the Cas12a-68 protease cleavage activity will be activated to cleave the gene fragment in the target region. Theoretically, because of the randomness of cleavage, the cleavage reaction has a ⅓ probability of making the base sequence in front of GFP in-frame, which allows GFP to be expressed and emit green fluorescence.

In the experiment, the four crRNA plasmid libraries were co-transfected with the Cas12a-68 pST1374 plasmid constructed in Example 1, respectively, into cells containing plasmid libraries with different PAM sequences. Puro antibiotic (puromycin, a protein synthesis inhibitor) was added for stress screening, and the cells were collected when the culture dish was full (about 6 days). Then, the cells were sorted, and the cells that could express the green fluorescent protein were collected. After that, the cells were broken, the genome was extracted, and four pairs of different primers were used to amplify the cleavage region fragment. The primer sequences are shown in Table 4. The PCR products were sent to Annoroad Gene Technology (Beijing) Co., Ltd. for second-generation sequencing, and then the sequencing results were analyzed.

TABLE 4

| primer | sequence (5'-3') |
|---|---|
| HG-crRNAseq-F | agtcaaaacctcccttctacgagcg (SEQ ID. NO. 12) |
| NNNA-crRNAseq-R1 | agctcctcgcccttgctcac (SEQ ID. NO. 13) |
| NNNT-crRNAseq-R2 | acttgaagctcctcgcccttgctcac (SEQ ID. NO. 14) |
| NNNG-crRNAseq-R3 | gatcagagctcctcgcccttgctcac (SEQ ID. NO. 15) |
| NNNC-crRNAseq-R4 | tagcttagctcctcgcccttgctcac (SEQ ID. NO. 16) |

According to the data of the second-generation sequencing, we analyzed the number of cleavage reactions under each PAM sequence and made a heat map. The darker the color, the higher the cleavage efficiency.

Figure 4:
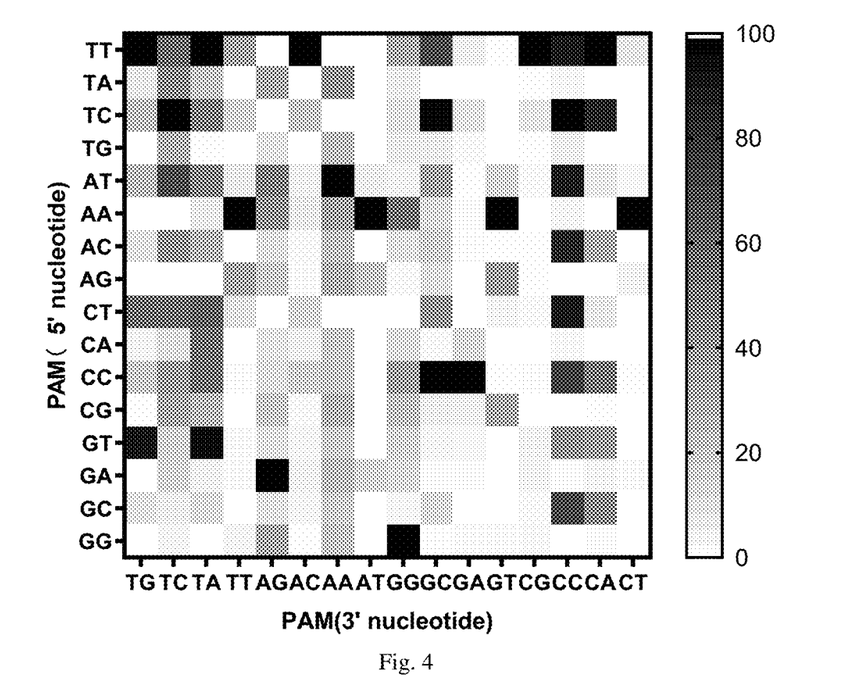
FIG. 4 is a diagram showing the effect of different PAM fragments on gene editing with a programmable nuclease in cells.

The results are shown in FIG. 4. According to the experimental results, besides the PAM sequence with LbCas12a TTTV, Cas12a-68 has a wider PAM recognition range, such as NYCC, TTCV, GTTR, AANT, CCGM, etc. (R represents A+G; Y represents C+T; M represents A+C; N represents A+C+G+T; and V represents A+C+G). The experimental results are shown in FIG. 4, which shows that the Cas12a-68 protease can exert its cleavage activity in mammalian cells, and has a wider PAM recognition range.

Example 4: Effect of Different Mutations of Cas12a-68 Protease on Cleavage Activity By analyzing the sequence conservation, we found the potential protease cleavage active sites D897 and E982. In order to verify whether the sites affect the cleavage activity of the Cas12a-68 protease, we constructed site mutation plasmids of D897A and E982A respectively on the basis of the Cas12-68 pET28a plasmid vector. The PCR primers for site mutation were synthesized, and the primer sequences are shown in Table 5. Then the plasmid vector was used as a template for PCR reaction, and the reaction products were used to transform DH5a competent cells. The monoclonal strains were selected, and then sent to be sequenced to identify whether the sites were mutated correctly.

TABLE 5

| primer | sequence (5'-3') |
|---|---|
| 68_D897A-F | TGTGAACATTATCGGCATCGCTCGTGGCGAGCGTAA TCT (SEQ ID. NO. 17) |
| 68_D897A-R | CGATGCCGATAATGTTCACATCAGAGCAGTCCTTCA CG (SEQ ID. NO. 18) |
| 68_E982A-F | TAAGGCAATCGTGGTCCTTGCAAATTTAAACGTGGG GTT (SEQ ID. NO. 19) |
| 68_E982A-R | CAAGGACCACGATTGCCTTATACTTTACAATCATCT TG (SEQ ID. NO. 20) |

Then two plasmid vectors with single site mutation were used to transform BL21 (DE3) competent cells to extract the protein containing site mutation. The Cas12a-68 site mutation protein was expressed in *E. coli*. The bacteria in the medium were collected, lysed by ultrasound, and purified by nickel column affinity chromatography with the target protein eluted with different concentrations of imidazole. The eluent was collected, and desalted by a desalting column, which could be used to detect the reaction.

According to the detection method of in vitro cleavage activity of proteases in Example 2, that is, in the experiment, crRNA consisted of a 21 nt region interacting with Cas12a and a 23 nt programmable guiding region for target DNA recognition. The target DNA was a gene fragment of the MERS virus (the gene sequence was shown as SEQ ID NO. 3). The target DNA fragment was amplified by PCR with forward and backward primers with Nco I and EcoR I enzymes respectively. Then the pET28a vector was double digested by Nco I and EcoR I. The digested vector and the PCR amplification product were reconnected under the action of the T4 ligase, and the ligation product was used to transform DH5a competent cells. The monoclonal strains were selected, and the fragment was identified to be correctly inserted into the vector by sequencing. Then the plasmid vector was extracted, and linearized with the EcoR V endonuclease for the detection reaction.

The detection system used was 400 ng of Cas12a-68-D897A or Cas12a-68-E982A (Cas12a-68-D897A was a sequence in which the $897^{th}$ amino acid of the wild-type Cas12a-68 amino acid sequence was mutated from aspartic acid into alanine, and the amino acid sequence was shown as SEQ ID NO. 4; and Cas12a-68-E982A was a sequence in which the $982^{nd}$ amino acid of the wild-type Cas12a-68 amino acid sequence was mutated from glutamic acid into alanine, and the amino acid sequence was shown as SEQ ID NO. 5), 100 ng of target DNA fragments (the gene fragment of MERS virus, the sequence of which was shown as SEQ ID NO. 3), and an amount of 5 pmol of crRNA, with the final volume of the reaction of 10 μL. The reaction was incubated at 37° C. for one hour, and heated at 95° C. for 5-10 minutes to inactivate the Cas12a protease. Then, agarose gel electrophoresis was performed to observe the cleaved target DNA molecules. Whether the site mutation protease had cleavage activity in vitro was verified.

Figure 5:
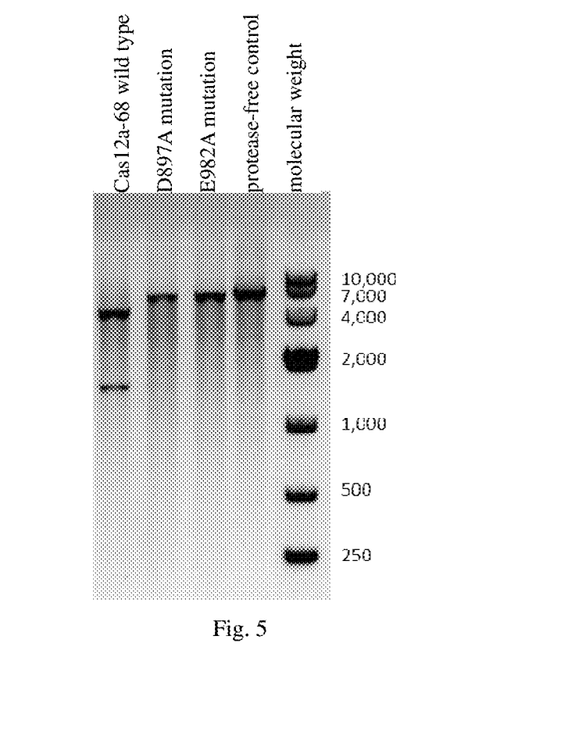
FIG. 5 is a detection diagram of the effect of different nuclease mutations on nuclease cleavage of double strands.

Conclusion: The experimental results are shown in FIG. 5, which shows that the two single point mutations of D897A and E982A lose their cleavage activity in vitro, indicating that D897 and E982 are critical for the cleavage activity of the Cas12a-68 protease.

The above is only the preferred embodiment of the present invention, but the protection scope of the present invention is not limited to this. Anyone skilled in the art can make equivalent replacements or changes according to the technical scheme of the present invention and the inventive concept thereof within the technical scope disclosed by the present invention, which should be all covered by the protection scope of the present invention.

The replacement Sequence Listing is in XML format and is hereby incorporated by reference. The name of the XML file is SEQ_LISTINGS_Replacement_File4 with the date of creation of Sep. 20, 2024 and size of 1,048,576 bytes. The replacement "Sequence Listing XML" does not include new matter

What is claimed is:

1. A vector comprising a polynucleotide, wherein the polynucleotide encodes a Cpf1 protein, and the Cpf1 protein comprises the amino acid sequence of as shown in SEQ ID NO: 1.

2. A gene editing method, comprising the following steps:
   (1) providing CRISPR RNA for a target gene sequence to be edited;
   (2) constructing a gene editing vector comprising an encoding gene sequence of the CRISPR RNA and a polynucleotide encoding a Cpf1 protein, wherein the Cpf1 protein comprises the amino acid sequence of as shown in SEQ ID NO: 1; and
   (3) introducing the gene editing vector in step (2) into a receptor cell to be gene edited, and screening to obtain a gene edited transgenic cell.

3. The method of gene editing of claim 2, wherein the CRISPR RNA comprises at least one of the sequence as shown in SEQ ID NOs: 7-10.

* * * * *